United States Patent [19]
Plaas et al.

[11] Patent Number: 4,551,139
[45] Date of Patent: Nov. 5, 1985

[54] METHOD AND APPARATUS FOR BURN WOUND TREATMENT

[75] Inventors: Jon R. Plaas, Lee's Summit, Mo.; Keith E. Parker, Olathe; James D. Keiser, Leewood, both of Kans.; Elmer C. Johnson, Jr., Raytown, Mo.

[73] Assignee: Marion Laboratories, Inc., Kansas City, Mo.

[21] Appl. No.: 346,920

[22] Filed: Feb. 8, 1982

[51] Int. Cl.[4] .................... A61M 11/00
[52] U.S. Cl. .................... 604/290; 604/289; 222/95; 222/96; 222/101; 222/105; 239/328; 239/329
[58] Field of Search .................... 604/24, 289, 310, 311, 604/290, 305, 149; 128/200.22, 200.23; 424/DIG. 15; 222/101-104, 93, 94, 96, 95, 99, 529, 386.5; 239/75, 329, 226, 328, 331, 332; 4/615-617

[56] References Cited

U.S. PATENT DOCUMENTS 542,688 7/1895 Shackleford .................... 4/616
711,045 10/1902 Gebauer .
753,990 3/1904 Lutje .
1,378,481 5/1921 Mobley .
2,631,757 3/1946 Alexander .
3,170,462 2/1962 Hall .
3,306,252 2/1967 Knight et al. .................... 128/200.23
3,428,224 2/1969 Eberhardt et al. .................... 222/529
3,761,590 9/1973 Fox, Jr. .................... 424/228
3,792,161 2/1974 Fox, Jr. .................... 424/228
3,874,381 4/1975 Baum .................... 128/206
4,136,802 1/1979 Mascia et al. .................... 222/95
4,162,042 7/1979 Mommsen .................... 239/526

FOREIGN PATENT DOCUMENTS

WO81/02094 8/1981 PCT Int'l Appl. .................... 222/96
142917 11/1953 Sweden .................... 239/328

OTHER PUBLICATIONS

"Tan Care", Coppertone, Mademoiselle, vol. 86, Jun. 1980, p. 9.
Boat Owners Association of the U.S., Consumer Equipment Guide, 1981, pp. 1, 54.
Denny et al., "A Preliminary Report on Spray Application of Topical Silver Sulfadiazine to Burn Wounds," J. of Trauma, 18, 730-731 (1978).

*Primary Examiner*—Henry J. Recla
*Assistant Examiner*—Karin M. Reichle

[57] ABSTRACT

An apparatus and method for spray application of a burn treating agent is disclosed. The apparatus delivers substantially all of the treating agent from a flexible source thereof through a spray nozzle, preferably without bringing the agent into contact with ambient air or contaminants. In a preferred embodiment, silver sulfadiazine cream is sprayed on a burn wound by urging the cream toward an outlet in a collapsible bag in which the cream is disposed by means of pressure applied to the exterior surface of the bag and conveying the cream from the outlet to a sanitary spray nozzle by means of a compressed air operated sanitary pump.

7 Claims, 2 Drawing Figures

METHOD AND APPARATUS FOR BURN WOUND TREATMENT

BACKGROUND OF THE INVENTION

Treatment of burn wounds has commonly involved direct topical application of an antimicrobial composition, such as silver sulfadiazine cream, which following application is covered by fine mesh gauze strips. This procedure is commonly painful to the patient, labor intensive, and time consuming. Alternatively, silver sulfadiazine cream has been impregnated into gauze which is then applied to the wound. This method is also painful, labor intensive and time consuming. Since contamination from the surrounding environment, either at the point of application or when the strips are impregnated is possible, extreme caution must be employed to maintain cleanliness.

Recently, spray application of cream or ointment for burn treatment has been tested as a relatively rapid and painless mode of cream application. Spray application was effected by directing an atomized spray of silver sulfadiazine cream (SSD) from a conventional small rigid container of sulfadiazine at a wound area from a distance of four to six inches employing a conventional air atomizing sprayer. This mode of application, though overcoming some problems associated with direct, hand application of treating agents and treatment of wounds with impregnated gauze, is not completely satisfactory. Specifically, the air employed in the method can introduce contaminants into the spray system which, over time, pose problems of wound sepsis.

More importantly, the prior art spray method tended to be intermittently painful for the patient due to uneven discharge of SSD cream from the sprayer with resultant painful high pressure air blasts against the wound site. Because it is viscous, SSD cream did not readily flow to the inlet of the pump system, but rather as the cream in the immediate area of the inlet was drawn into the pump, a void or "rathole" containing no cream was created. During the period when the pump inlet is in such a void, air is introduced into the pump flow course, subsequently causing breaks in delivery of SSD spray and producing the above-noted painful air delivery against the wound.

Furthermore because SSD cream is viscous, the prior art spray method resulted in substantial waste of SSD. That is, not all of the cream in the rigid prior art containers flowed to the pump inlet, but rather substantial residues of SSD cream remained on the sides and bottom edges of the containers.

It has now been discovered that problems relating to sepsis during topical burn treatment can be satisfactorily overcome by means of a spray applicator system which maintains the burn agent in isolation from ambient conditions, particularly by means of a compressed air operated sanitary pump and nozzle. More significantly, it has been discovered that a conventional silver sulfadiazine cream can be sprayed upon burn wounds with minimal patient discomfort, without intermittent delivery of air and with minimal waste of the cream. Spraying of silver sulfadiazine cream on gauze is also effectively achieved by means of the present invention.

BRIEF SUMMARY OF THE INVENTION

This invention relates to an apparatus and method for spray application of a topical burn treating agent and has particular utility with respect to highly viscous creams, such as conventional silver sulfadiazine cream. The apparatus comprises a flexible container or source of the treating agent;

a spray nozzle;

means for delivering the treating agent to an outlet from the container; and means for conveying a pressurized flow of treating agent from the outlet in the source to the spray nozzle in a conduit flow course, which is preferably isolated from ambient air.

The method comprises conveying an uninterrupted pressurized flow of burn treating agent from a collapsible reservoir of the treating agent through a spray nozzle under sanitary conditions, preferably while maintaining the treating agent in isolation from ambient air.

In preferred practice silver sulfadiazine cream is sprayed on a wound or gauze strips employing a compressed air operated sanitary pump and spray nozzle. The cream is contained in a collapsible bag disposed on a support such that its outlet is at the lower end thereof. The bag outlet is attached to the pump suction end or inlet. A weighted member, preferably a roller, is disposed at the other, higher end of the bag. The weight urges the silver sulfadiazine cream toward the outlet due to gravitational forces, thus continuously delivering the cream to the pump inlet.

DETAILED DESCRIPTION

Figure 1:
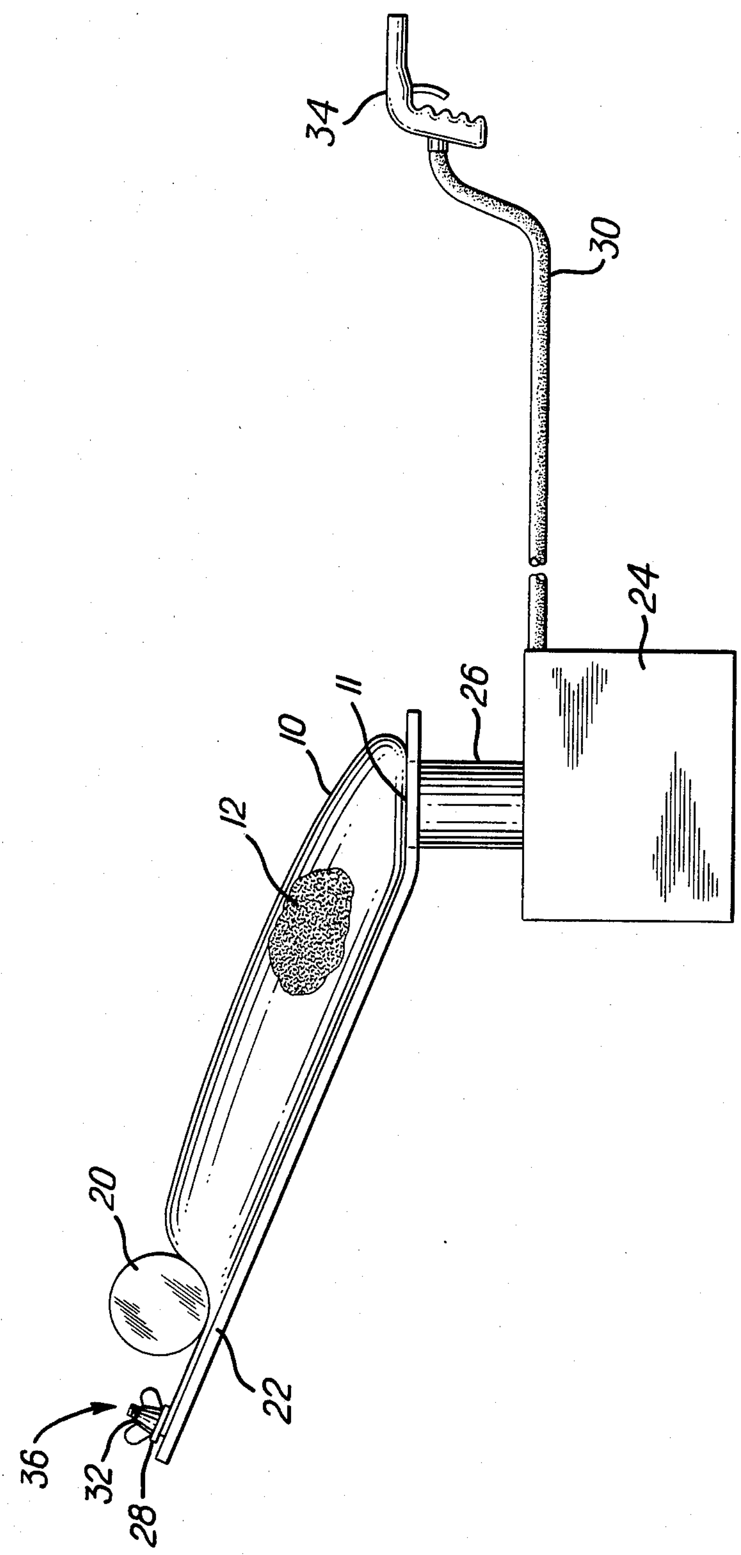
FIG. 1 is a side view of a preferred embodiment of the apparatus of the invention.

The present invention provides a method and means for spray application of topical treating agents. By means of the invention relatively painless application can be effected while reducing potential for wound contamination as a result of the mode of application.

The present invention may be employed to apply any topical burn treating agent, and is most suitable for application of burn treating creams and ointments. The invention has particular utility in the application of topical antimicrobial agents, specifically silver sulfadiazine cream. Silver sulfadiazine creams having viscosities ranging from 60,000 to 2,000,000 cps may be employed in the invention. Those having an average viscosity of about 250,000 cps are preferred.

SILVADENE, a silver sulfadiazine cream sold by Marion Laboratories, Inc. (Kansas City, Missouri) is representative of a particularly preferred composition for application in accordance with the invention and the invention is described hereinbelow with reference to application of such a preferred composition. Such description is by way of example only and it is to be understood that other topical treating agents may be used in the practice of the invention.

In the practice of the present invention the silver sulfadiazine cream is confined in a flexible container or reservoir to provide a source from which the cream can be drawn for application. Since silver sulfadiazine is itself an antimicrobial agent, no steps need be taken to create an aseptic condition in the container. With other types of materials care must be taken to maintain them in a sterile condition in the source container or reservoir in order to avoid contamination.

The container for the silver sulfadiazine cream must be flexible and is optimally fully collapsible. The flexibility is necessary to permit complete discharge of the cream without air gaps.

In practice, the cream is delivered without interruption to an outlet in the container by contracting the container in whole or in part. As a result of the contraction, silver sulfadiazine cream is always present at the outlet and air gaps, with consequent painful pressurized air flow against a burn wound, are eliminated. In view of this intended purpose of the container's flexibility, the container employed must have flexibility sufficient to permit contraction of the container such that no voids are created by removal of the cream from the container. For purposes of the present invention, flexible containers are to be understood to include any container which contracts in the above-defined manner.

Delivery of the cream to the container outlet can be achieved by application of pressure to the exterior surface of a flexible container. Such delivery can be effected by placing the container, preferably a flexible, readily collapsible bag, on a support and engaging a member with the unsupported side of the container. The member can be urged by appropriate means, toward the outlet in the bag from a position at the opposite end thereof.

The means for urging the member toward the outlet can be gravitational force where a weighted member is employed and the outlet is disposed at the lower end of the container. In this case, the weighted member must be of a size and weight sufficient to cause contraction of the container in an amount adequate to prevent voids in the container due to discharge of cream from the container. Weighted members for purposes hereof are limited to those which can achieve such effect.

In a preferred embodiment the weighted member is a roller or rolling member which is at least as wide as the container and which is placed at the upper end of an angled support upon which a readily collapsible container of cream is received with its outlet disposed at its lower end. Gravity forces the roller against the container, causing it to collapse as cream is discharged, thus delivering cream to the container outlet without interruption.

Application of silver sulfadiazine cream is effected by delivering the cream to an outlet from the flexible container and conveying a pressurized flow of the cream from the container outlet to a spray nozzle through a conduit flow course, which is optimally isolated from ambient air. For this purpose a sanitary pump operated by compressed air may be connected on its suction end to the outlet of a flexible container, and on its other end to a sanitary spray nozzle. The pump pressure must be sufficient to deliver a pressurized flow of the treating agent to the nozzle. The spray nozzle converts the pressurized flow to a spray, the particles of which have a velocity low enough to produce minimal pain when directed against a burn wound area. The wound thus treated may then be covered with gauze dressings. Alternatively, the spray may be applied to gauze strips which are then applied to the burn wound.

In order to minimize potential for contamination, it is preferred that the equipment employed be that which can readily be sterilized. Thus, sanitary pumps and spray guns which can be readily disassembled and cleaned are preferred. Materials employed in the equipment are preferably polished stainless steel or the like which can be autoclaved and have few crevices which would pose cleaning problems. In order to avoid cross-contamination when the spray system is employed on different patients, one may simply change spray guns or nozzles between applications. When the cream is an antimicrobial and the flow course is isolated from environmental air, no contaminants are introduced into the wound in conjunction with the treating agent. Thus risks of burn wound contamination associated with other modes of topical treatment are virtually eliminated.

In effecting treatment, the spray pattern should not cover too wide an area in order to avoid overspraying and the messiness associated therewith. Desirably, the spray pattern should cover an area of about 3 inches to 6 inches in width when the nozzle is positioned about one foot from a wound. Where a silver sulfadiazine cream having a viscosity as above described is employed, the pump delivery pressure in the flow course can vary between 200 psi and 600 psi.

However, the spray delivery from the nozzle should be such that, upon impacting a wound surface, pain is minimized. The velocity and size of the spray particles are directly related to the pain level experienced by the patient. The velocity can be modified by changing the degree of atomization by manipulating the size of the orifice and the angle of the spray nozzle. For example, by increasing atomization, (i.e. reducing spray particle size) velocity is reduced resulting in reduced pain upon spray delivery at the wound site. As used herein, references to delivery of low pressure atomized sprays means sprays, the particle size and velocity of which have been reduced to produce minimal pain upon impact at a wound site. It has been found that when operating an airless pump in accordance with the invention in the pressure ranges noted above using silver sulfadiazine creams, the elliptical nozzle of a Graco airless handheld gun having a 0.002 inch diameter orifice and an 11° spray angle delivers the desired 4 to 6 inch spray pattern from one foot while delivering an atomized spray the particle size and velocity of which results in minimal pain upon application to a burn wound.

Figure 2:
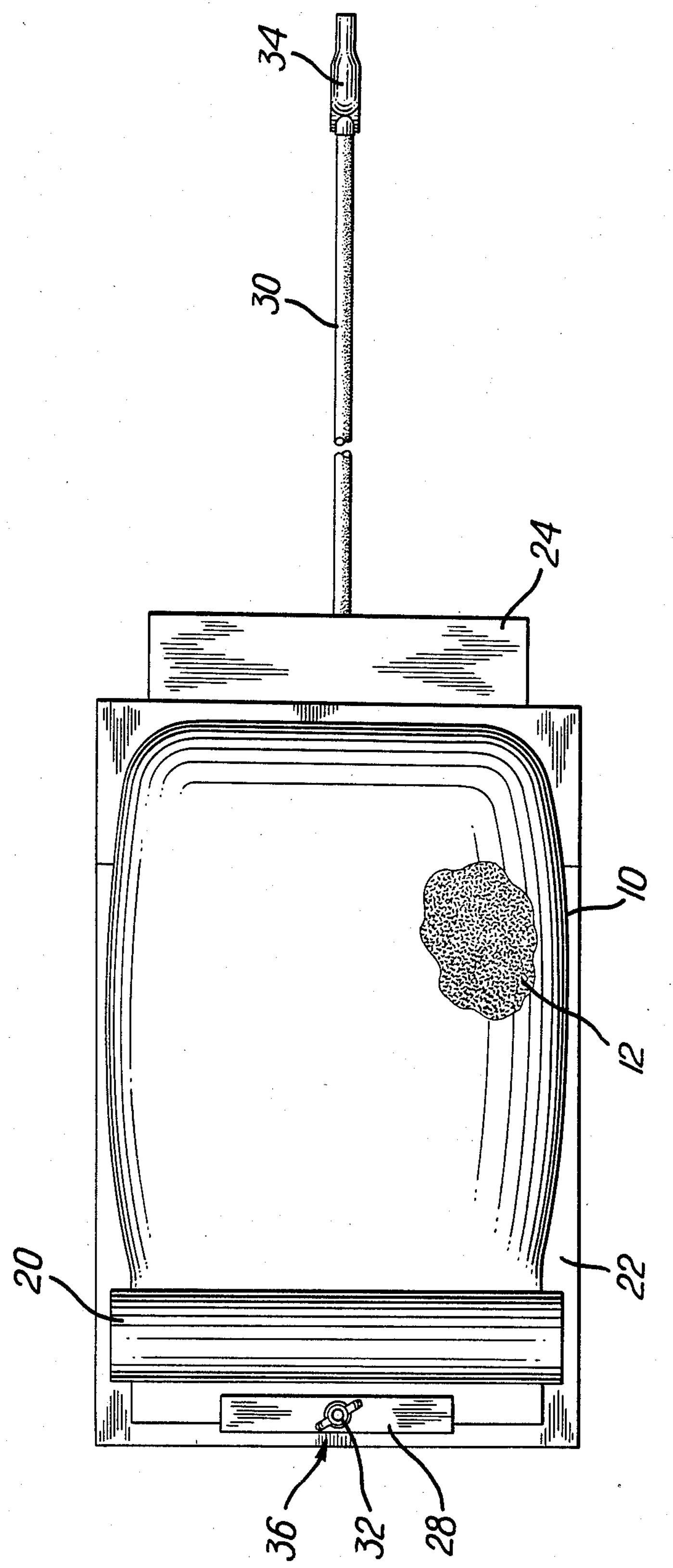
FIG. 2 is a top view of the apparatus.

The apparatus of the invention will be more fully understood by reference to the accompanying drawings which depict the preferred embodiment of the invention. In FIG. 1 and FIG. 2, a flexible container 10 of the treating agent 12, in preferred form, a silver sulfadiazine cream is provided with outlet 11. The container 10 preferably is a generally elongated, flexible, readily collapsible bag structure made of high strength synthetic material such as polyethylene and having a metallized coating on the outside to render the bag opaque and thereby protect the contents from adverse effects of light. The treating agent is delivered to outlet 11 by means of a weighted member, as shown in preferred form by roller 20. The bag 10 is received on support 22 positioned at an angle such that gravitational forces will cause roller 20 to work against the bag to thereby urge the contents thereof toward outlet 11. Bag 10 is held to support 22 by attachment means generally designated 36. Attachment means 36 may comprise a rigid plate 28 held in tight engagement with the upper end of bag 10 by means of wing nut and screw 32. The treating agent 12 is delivered to the suction side of pump unit 24 through conduit 26. Pump unit 24 is a conventional form of sanitary pump, preferably one which is operated by compressed air, for example Graco's Monarch 5:1 Ratio Airless Sanitary Pump.

Graco's pump may be operated so that the air pressure supplied for operation thereof will be multiplied in a ratio of about 5:1 relative to pressure delivered by the pump. In other words, if the air pressure is in the range of 40 to 120 psi, the pump will deliver a flow of silver sulfadiazine cream at a pressure in the range of about 200–600 psi. The cream pumped by the pump unit 24 will be delivered through conduit 30, which may be a flexible hose, to spray nozzle 34. Spray nozzle 34 includes a control to permit conversion of the high pressure flow to an atomized spray discharge of gentle nature which can be directed against the wound being treated. Graco's sanitary airless hand-held spray gun of stainless steel is a suitable spray nozzle.

The entire flow course from container 10 to nozzle or gun 34 may be sterilized prior to use and connected in a manner which isolates the treating agent from the treating environment. Therefore from outlet 11 until the treating agent is delivered at the spray nozzle 34 there is no contact of the ointment with environmental air and no contaminants can be introduced into the system.

Burn treatment is effected by holding the spray nozzle above the wound so that the treating agent spray can be directed quickly, conveniently and relatively painlessly against the wound surface. Following the treatment of the wound by the building up of a film of treating agent thereon dressings may be applied. The amount of treating agent applied might be measured by employing a stroke counter on the pump system.

Since patients in a burn unit are at high cardiac risk, amperage leakage from the pump system should be eliminated. An isolation transformer, 2.0 KVA wired 1:1 has been found to eliminate amperage leaks from the compressor motor used with the Graco pump. Further it has been found desirable to employ an EMI filter to avoid interference with hospital monitoring instruments.

As has been noted earlier, use of the preferred embodiment of the method and apparatus of this invention permits treatment of burn wounds in a manner which greatly lessens the potential for contamination of the wounds, since no contaminating agency is allowed to come into contact with the treating agent or application apparatus. Since the container of treating agent is isolated from the environment, there is no need to discard its contents after application to a single patient. Rather, the container can provide a large reservoir of treating agent for use in an entire burn unit, thus minimizing waste. Further, no extreme measures are required to maintain the treating agent and spray system in a sterile condition. Moreover, the invention permits rapid, relatively painless treatment of patients in a non-labor intensive manner.

We claim:

1. A method for spray application of a burn treating agent comprising:

(a) delivering a viscous cream or ointment burn treating agent to an outlet in a flexible container of the treating agent without interruption;

(b) pressurizing a flow of the treating agent from the outlet to a spray nozzle in a conduit flow course;

(c) reducing the pressure of the pressurized flow in the nozzle to provide an atomized spray of agent; and (d) delivering said low pressure atomized spray of agent from the nozzle against a burn wound surface.

2. The method of claim 1, in which the treating agent is delivered to the outlet by application of pressure to the exterior surface of the container.

3. The method of claim 1 in which the conduit flow course is isolated from ambient air.

4. The method of claim 1 wherein the burn treating agent is a silver sulfadiazine cream.

5. The method of claim 4 wherein the silver sulfadiazine cream has a viscosity of 60,000 cps to 2,000,000 cps.

6. The method of claim 5 wherein the silver sulfadiazine cream has a viscosity of about 250,000 cps.

7. The method of claim 1 wherein the treating agent is conveyed from the reservoir to the spray nozzle at a pressure of about 200 psi to 600 psi.

* * * * *